United States Patent [19]

Dabney

[11] Patent Number: 5,787,892
[45] Date of Patent: Aug. 4, 1998

[54] ANAL ORGASM MONITOR

[76] Inventor: James Conway Dabney, 2125 Wrens Way, Clearwater, Fla. 34624

[21] Appl. No.: 574,208

[22] Filed: Dec. 18, 1995

[51] Int. Cl.⁶ .................................................. A61B 5/103
[52] U.S. Cl. .......................... 128/780; 128/778; 606/197
[58] Field of Search ............................. 128/748, 774, 128/777, 780; 606/193, 197

[56] References Cited

U.S. PATENT DOCUMENTS

| | | | |
|---|---|---|---|
| 899,477 | 9/1908 | Williams | 606/197 |
| 2,168,427 | 8/1939 | McConkey | 606/197 |
| 4,953,563 | 9/1990 | Kaiser et al. | 128/780 |
| 5,005,586 | 4/1991 | Lahr | 606/197 |
| 5,061,239 | 10/1991 | Sheils | 606/197 |

*Primary Examiner*—Max Hindenburg

[57] ABSTRACT

A device for determining the contractions of an anal sphincter and associated muscles comprising a core formed in a generally cylindrical configuration from a relatively rigid plastic material having a distal end and a proximal end, the core having a central section of a reduced diameter and an axial length, sheet material formed of a flexible essentially inelastic plastic material with an adhesive securing the sheet material to the core and a head adjacent to the distal end of the core, the proximal end of the head being located adjacent to the distal end of the central section and with the distal end of the head being of a reduced diameter.

11 Claims, 4 Drawing Sheets

ANAL ORGASM MONITOR

BACKGROUND OF THE INVENTION

1. Field of the Invention

The present invention relates to an anal orgasm monitor and more particularly pertains to determining the contractions of an anal sphincter and associated muscles during an orgasm.

2. Description of the Prior Art

The use of probes, sensors and monitors is known in the prior art. More specifically, probes, sensors and monitors heretofore devised and utilized for the purpose of sensing properties of a body for various purposes are known to consist basically of familiar, expected, and obvious structural configurations, notwithstanding the myriad of designs encompassed by the crowded prior art which has been developed for the fulfillment of countless objectives and requirements.

By way of example, the prior discloses in U.S. Pat. No. 4,216,783 to Kaiser et al., a pneumatic monitor for indicating strength of contractile muscles.

U.S. Pat. No. 3,926,178 to Feldzamen discloses an apparatus for aiding the voluntary exercising of sphincter muscles.

U.S. Pat. No. 5,433,216 to Sugrue et al., discloses an intra-abdominal pressure measurement apparatus and method.

U.S. Pat. No. 5,005,586 to Lahr discloses a method for exercising a patient's anal canal.

U.S. Pat. No. 3,625,199 to Summers discloses an implantable pressure indicator.

Lastly, European Patent Number 50,983 discloses a patient anaesthesia depth monitoring system.

In this respect, the anal orgasm monitor according to the present invention substantially departs from the conventional concepts and designs of the prior art, and in doing so provides an apparatus primarily developed for the purpose of determining the contractions of an anal sphincter and associated muscles during an orgasm.

Therefore, it can be appreciated that there exists a continuing need for new and improved anal orgasm monitor which can be used for determining the contradictions of an anal sphincter and associated muscles during an orgasm. In this regard, the present invention substantially fulfills this need.

SUMMARY OF THE INVENTION

In view of the foregoing disadvantages inherent in the known types of probes, sensors and monitors now present in the prior art, the present invention provides an improved anal orgasm monitor. As such, the general purpose of the present invention, which will be described subsequently in greater detail, is to provide a new and improved anal orgasm monitor and method which has all the advantages of the prior art and none of the disadvantages.

To attain this, the present invention essentially comprises a An anal orgasm monitor for determining the contractions of an anal sphincter and associated muscles during an orgasm, comprising, in combination a core formed in a generally cylindrical configuration from a relatively rigid plastic material having a distal end and a proximal end with an axial length of about 4 inches, the core having a central section of a reduced diameter of about ⅞ inch and an axial length of about 1½ inches, the central section having an anular sheet of inelastic flexible material for sensing change of pressure thereon, a head ajdacent to the distal end of the core, the proximal end of the head being located adjacent to the distal end of the central section with a diameter of about 1.5 inches and with the distal end of the head being of a reduced diameter to form a generally cone-shaped configuration, a tail adjacent to the proximal end of the core, the distal end of the tail being located at the proximal end of the central section with a diameter of about 1½ inches, the proximal end of the head at the distal end of the tail being spaced by about 1½ inches, a first axial aperture and a second axial aperture, each aperture extending through the proximal end of the core, an air outlet tube having a proximal end remote from the core and a distal end coupled to the second axial aperture for allowing the removal of air from the region of the core adjacent to the sheet, a transducer coupled to the proximal end of the water inlet tube with an associated fill tube and inlet valve to allow the selective adding of water to the inlet tube and core and the calibration of the transducer to atmospheric pressure, an outlet valve at the proximal end of the air outlet tube to allow the escape of air from the core and associated tubes during the filling of the core with water and for closing off the air outlet tube when the tubes and core are full of water and an electronic monitor coupled to the transducer whereby pressure variations on the central section as caused by an anal sphincter and associated muscles during orgasm will provide a display of variations in pressure sensed by the central section of the core.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved orgasm monitor which has all the advantages of the prior art probes, sensors and monitors and none of the disadvantages.

It is another object of the present invention to provide a new and improved orgasm monitor which may be easily and efficiently manufactured and marketed.

It is further object of the present invention to provide a new and improved anal orgasm monitor which is of a safe, durable and reliable construction.

An even further object of the present invention is to provide a new and improved anal orgasm monitor which is susceptible of a low cost of manufacture with regard to both materials and labor, and which accordingly are then susceptible of low prices of sale to the consuming public, thereby making such anal orgasm monitor economically available to the buying public.

Even still another object of the present invention is to determine the contractions of an anal sphincter and associated muscles during an orgasm.

Lastly, it is an object of the present invention to provide a new and improved a device for determining the contractions of an anal sphincter muscle comprising: a core formed in a generally cylindrical configuration from a relatively rigid plastic material having a distal end and a proximal end, the core having a central section of a reduced diameter and an axial length, sheet material formed of a flexible essentially inelastic plastic material with an adhesive securing the sheet material to the core and a head adjacent to the distal end of the core, the proximal end of the head being located adjacent to the distal end of the central section and with the distal end of the head being of a reduced diameter.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
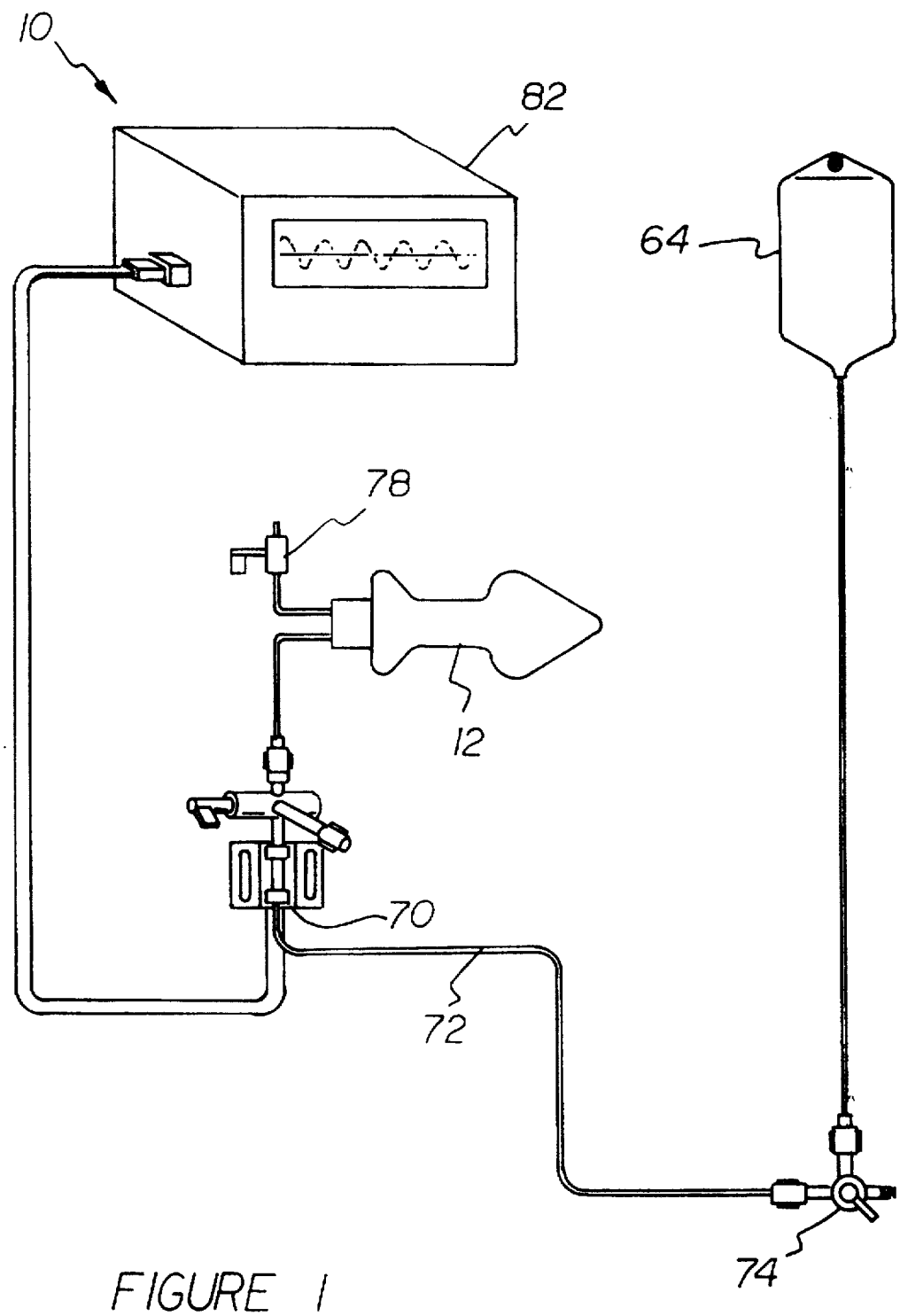
FIG. 1 is a perspective illustration of the preferred embodiment of the anal orgasm monitor constructed in accordance with the principles of the present invention.
Figure 2:
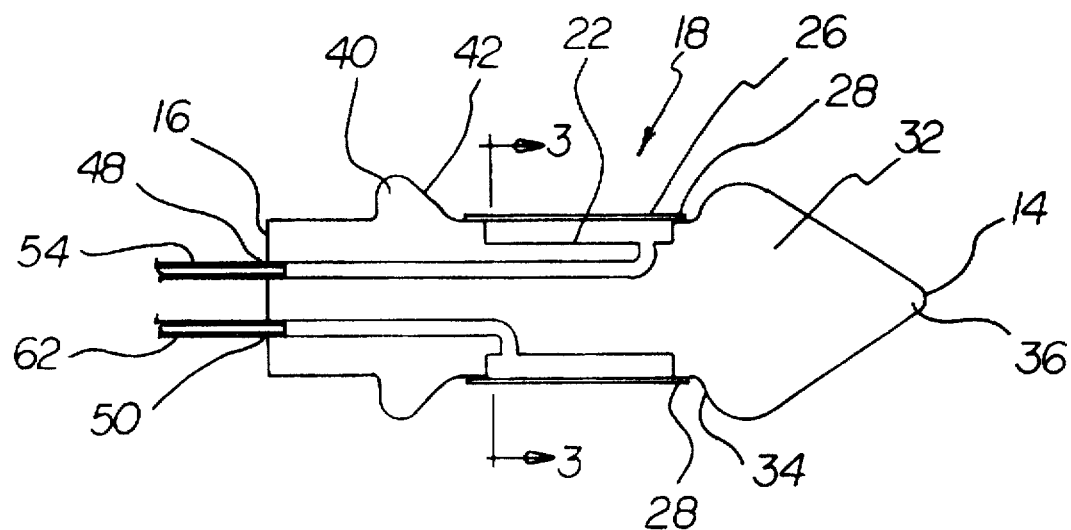
FIG. 2 is an enlarged cross-sectional view of the core shown in FIG. 1.
Figure 3:
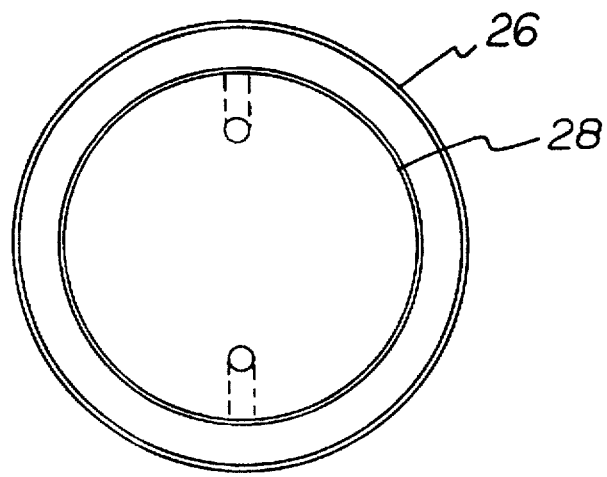
FIG. 3 is a cross-sectional view taken along line 3—3 of FIG. 2.

With reference now to the drawings, and in particular to FIG. 1 thereof, the preferred embodiment of the new and improved anal orgasm monitor embodying the principles and concepts of the present invention and generally designated by the reference numeral 10 will be described.

The present invention, the new and improved anal orgasm monitor is comprised of a plurality of components. Such components in their broadest context include a core, windows, a head and a tail. Such components are individually configured and correlated with respect to each other so as to attain the desired objective.

More specifically, the present invention may be considered as a system 10. The central component of such a system is a core 12. The core is formed of a generally cylindrical configuration. It is fabricated of a relatively rigid plastic material, preferably polyethylene terepthalate (PET). It has a distal end 14 and a proximal end 16. The core also has an axial length of about 4 inches. The core has a central section 18 of a reduced diameter of about ⅞ inch. The axial length of the central section is about 1½ inches.

The central section is formed with an annular recess 22. Such recess has a generally rectangular cross-sectional configuration.

Next provided is an annular sheet 26. The sheet material is preferably of a flexible, essentially inelastic material, preferably polyethylene. Such material is in a generally annular configuration over the central section of the core. It is located so as to overlie the recess. An adhesive 28 is used for securing the material to the core peripherally at its axial edges.

The plastic sheet material functions as a diaphragm for changing shape in response to applied pressure as through the anal sphincter muscle.

Next provided as a component of the system 10 is a head 32. The head is located adjacent to the distal end of the core. The proximal end 34 of the head is located adjacent to the distal end of the central section. The head has a diameter at its largest point, adjacent to the proximal end, of about 1.5 inches. The distal end 36 of the head is of a reduced diameter to form a generally cone-shaped configuration. The design of the head is to facilitate insertion and, in combination with the tail, to maintain the proper position of the central section during operation and use.

Complimentary to the head is a tail 40. The tail functions as a barrier to preclude excess insertion of the core into the anal canal. The tail is located adjacent to the proximal end of the core. The distal end 42 of the tail is located at the proximal end of the central section. It has a diameter of about 1½ inches at its widest point. The proximal end of the tail and the distal end of the core are spaced by about 1½ inches.

Formed in the core is a first axial aperture 48 and a second axial aperture 50. The apertures extend through the proximal end of the core.

In association with the first aperture, there is provided an air outlet tube 54. Such tube has a proximal end remote from the core. It also has a distal end coupled to the core at the second axial aperture.

A water inlet tube 62 is then provided. Such water inlet tube has a proximal end remote from the core and it also has a distal end coupled to the first axial aperture.

Located remote from the core 12 and at an elevated location is a bag 64 for a supply of fluid, preferably water, for use in filling the core. The water from the bag enters the region of the recess beneath the sheet material through a line coupled to the water inlet tube while the air from the recess beneath the sheet material through a line coupled to the air outlet tube. Coupling of such lines to the recess are at axially spaced locations to facilitate the smooth flow of water and air during the filling process.

A transducer 70 is then coupled to the proximal end of the water inlet tube. It has an associated fill tube 72 and an inlet valve 74. This allows the selective adding of water to the inlet tube and core. The valve when closed also allows for sealing of water within the tube and core.

An outlet valve 78 is next provided at the proximal end of the air outlet tube. Such outlet tube valve allows the escape of air from the core and associated tubes during the filling of the core with water. The valve also functions to close off the air outlet tube when the tubes and core are full of water.

Lastly, provided is an electronic monitor 82. Such monitor may take the form of a cathode ray tube. Such monitor is coupled to the transducer electronically. In this manner, pressure variations on the central section of the core, as caused by an anal sphincter during orgasm, will cause a change of pressure at the transducer and a resulting electrical pulse or pulses to the monitor to thereby provide a display. Such display exhibits the variation in pressure by the central section of the probe during operation and use.

Figure 4:
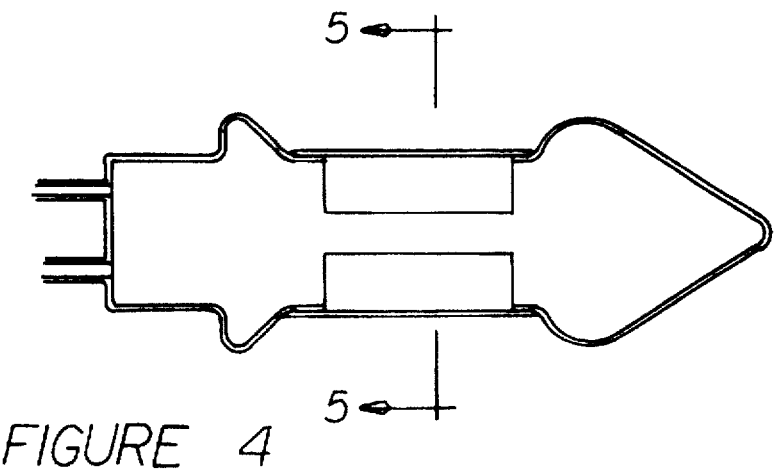
FIG. 4 is a cross-sectional view of a core constructed in accordance with an alternate embodiment of the invention.
Figure 5:
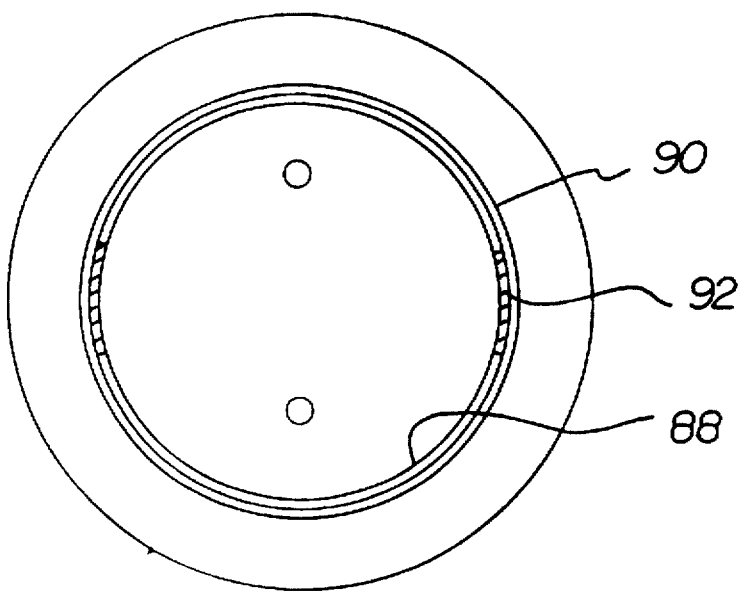
FIG. 5 is a cross-sectional view taken along line 5—5 of FIG. 4.

In an alternate embodiment of the invention as shown in FIGS. 4 and 5, the recess is not utilized. In place thereof, the entire core is filled with water and apertures 88 are formed in the central section of the core. Sheet material 90 constituting windows is in an annular configuration to cover the central section and apertures. An adhesive 92 adheres the sheet material to the core around the apertures.

Figure 6:
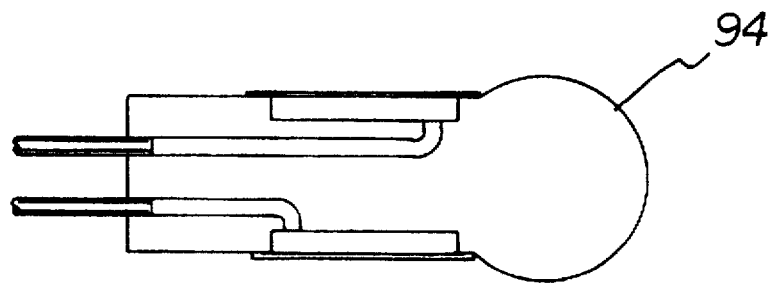
FIG. 6 is an enlarged cross-sectional view of a core constructed in accordance with another alternate embodiment of the invention.
Figure 7:
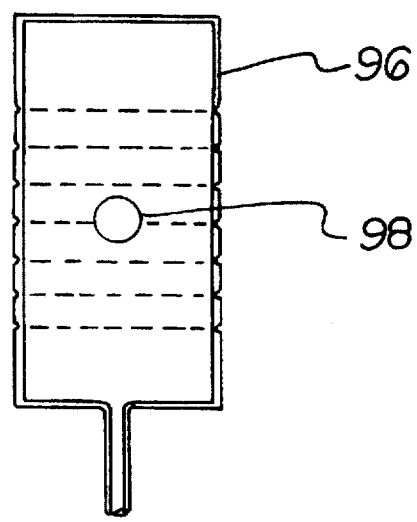
FIG. 7 is a front elevational view of a manometer as used as an alternative to the cathode ray tube of FIG. 1.

FIG. 6 illustrates another alternate embodiment of the invention. In such embodiment no tail it utilized. Further, the head 94 is of an enlarged, generally ball-shaped configuration. Such embodiment is for vaginal use. Lastly, FIG. 7 illustrates an alternate monitor. Such alternate monitor is a manometer 96 with a fluid line at its bottom coupled to the core preferably through the water inlet line. A ball 98 floats on the water line. The ball will thus rise and fall with changes of pressure caused by the core. Indicia lines are preferably formed on the surface of the manometer.

The anal sensor or core of the present invention consists of an enclosed fluid filled cylinder. It has an insertion or head end, a sensing area or body, and a tail or barrier to limit insertion of the sensor into the anal canal.

The head is conical in shape. The apex of the cone is slightly rounded on its tip to enable gentle insertion into the anal canal. The base of the cone which is attached to the body has a circumference that is greater than the body of the sensor. The diameter of the base of the cone is approximately ½ inch greater than the diameter of the body. The body or sensing area is approximately 1½ inches long and has a diameter of about ⅞ inch or slightly less. The diameter of the barrier or tail is at least ½ inches greater than the body. Its purpose is to limit further penetration into the anal canal.

The sensor area consists of either an annular recess or two windows running the length of the body symmetrically located on either side of the body and occupying approximately 75 percent of the body surface area in the central section. The body in that central section is then covered with a flexible sheet, preferably a vinyl, making such area a sensing diaphragm.

The anal sensor and the cylinder, is totally sealed except for two flexible, but relatively rigid polyvinyl tubes which are inserted through the tail of the sensor and are distal to the barrier. One of the tubes connects the sensor to a transducer. The other is used to fill the sensor, transducer and interconnecting polyvinyl tube with water. It is then sealed, leaving watertight sensor which is attached to the transducer with rigid and flexible polyethylene tubing.

For insertion into the anal canal, the head is lubricated and gently passed through the anal canal. Once the head passes through the canal, the anal sphincter surrounds the body, the sensing area of the instrument. The enlarged barrier prevents further penetration. This position in the sphincter is maintained by the enlarged head and the barrier which retard further motion. The sensor can be removed at any time by gentle traction on its tail.

The diaphragm or central are of the sensor transmits impulses via the polyvinyl tubing to the transducer which are then amplified and displayed on a monitoring device. The diaphragem responds to all changes of muscle tone of the anal sphincter and the monitor displays a graphic and quantitative analyses of the sphincter contraction before, during and after orgasm.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An anal orgasm monitor for determining the contractions of an anal sphincter and associated muscles during an orgasm and sexual arousal, comprising, in combination:

a core formed in a generally cylindrical configuration from a relatively rigid plastic material having a distal end and a proximal end with an axial length of about 4 inches, the core having a central section of a reduced diameter of about ⅞ inch and an axial length of about 1½ inches, the central section having an annular sheet of inelastic flexible material for sensing change of pressure thereon;

a head adjacent to the distal end of the core, the proximal end of the head being located adjacent to the distal end of the central section with a diameter of about 1.5 inches and with the distal end of the head being of a reduced diameter to form a generally cone-shaped configuration;

a tail adjacent to the proximal end of the core, the distal end of the tail being located at the proximal end of the central section with a diameter of about 1½ inches, the proximal end of the head at the distal end of the tail being spaced by about 1½ inches;

a first axial aperture and a second axial aperture, each aperture extending through the proximal end of the core;

a water inlet tube having a proximal end remote from the core and a distal end coupled to the first axial aperture;

an air outlet tube having a proximal end remote from the core and a distal end coupled to the second axial aperture for allowing the removal of air from the region of the core adjacent to the sheet;

a transducer coupled to the proximal end of the water inlet tube with an associated fill tube and inlet valve to allow the selective adding of water to the inlet tube and core and the calibration of the transducer to atmospheric pressure;

an outlet valve at the proximal end of the air outlet tube to allow the escape of air from the core and associated tubes during the filling of the core with water and for closing off the air outlet tube when the tubes and core are full of water; and an electronic monitor coupled to the transducer whereby pressure variations on the central section as caused by an anal sphincter during orgasm will provide a display of variations in pressure sensed by the central section of the core.

2. A device for determining the contractions of a muscle comprising:

a core formed in a generally cylindrical configuration from a relatively rigid plastic material having a distal end and a proximal end, the core having a central section of a reduced diameter and an axial length, the core having a water inlet and air outlet;

sheet material formed of a flexible essentially inelastic plastic material with an adhesive securing the sheet material to the core; and a head adjacent to the distal end of the core, the proximal end of the head being located adjacent to the distal end of the central section and with the distal end of the head being of a reduced diameter.

3. The device as set forth in claim 2 and further comprising:

a tail adjacent to the proximal end of the core, the distal end of the tail being located at the proximal end of the central section.

4. The device as set forth in claim 2 wherein the head is of a generally cone-shaped configuration.

5. The device as set forth in claim 2 wherein the head is of a generally spherical configuration.

6. The device as set forth in claim 2 and further comprising:

a water inlet tube having a proximal end remote from the core and a distal end coupled to an axial aperture of the water inlet of the core; and a sensor coupled to the proximal end of the water inlet tube with an associated fill tube and inlet valve to allow the selective adding of water to the inlet tube and core.

7. The device as set forth in claim 6 wherein the sensor has associated therewith an electronic monitor for observing sensed pressure variations.

8. The device as set forth in claim 6 wherein the sensor has associated therewith a manometer for observing sensed pressure variations.

9. The device as set forth in claim 2 and further comprising:

a first axial aperture and a second axial aperture extending through the water inlet and air outlet of the core respectively; and an air outlet tube coupled with the second axial aperture; and an outlet valve at the proximal end of the air outlet tube to allow the escape of air from the core and associated tubes during the filling of the core with water and for closing off the air outlet tube when the tubes and core are full of water.

10. The device as set forth in claim 2 wherein the central section of the core is formed with an annular recess with the sheet material secured thereover.

11. The device as set forth in claim 2 wherein the central section of the core is formed with apertures with the sheet material secured thereover.

* * * * *